(12) United States Patent
Burnie et al.

(10) Patent No.: US 7,037,495 B1
(45) Date of Patent: May 2, 2006

(54) ANTIMICROBIAL COMPOSITIONS

(75) Inventors: James P Burnie, Alderley Edge (GB); Ruth C Matthews, Alderley Edge (GB)

(73) Assignee: NeuTec Pharma plc, Manchester (GB)

( * ) Notice: Subject to any disclaimer, the term of this patent is extended or adjusted under 35 U.S.C. 154(b) by 546 days.

(21) Appl. No.: 10/110,136

(22) PCT Filed: Oct. 9, 2000

(86) PCT No.: PCT/GB00/03866

§ 371 (c)(1),
(2), (4) Date: Jul. 24, 2002

(87) PCT Pub. No.: WO01/27280

PCT Pub. Date: Apr. 19, 2001

(30) Foreign Application Priority Data

Oct. 9, 1999 (GB) .................................... 9923858

(51) Int. Cl.
*A61K 39/00* (2006.01)
*A61K 39/395* (2006.01)
*A01N 37/18* (2006.01)

(52) U.S. Cl. ................................ 424/130.1; 424/184.1; 514/2

(58) Field of Classification Search ............. 424/130.1, 424/184.1; 514/2
See application file for complete search history.

(56) References Cited

U.S. PATENT DOCUMENTS 4,740,372 A * 4/1988 Boncic .................... 424/94.64
5,116,615 A * 5/1992 Gokcen et al. ............ 424/94.2
5,698,178 A    12/1997 Goldenberg
6,228,323 B1 * 5/2001 Asgharian et al. ............ 422/28

FOREIGN PATENT DOCUMENTS

WO   WO 96/33285   10/1996

OTHER PUBLICATIONS

Burnie et al., "Defining potential targets for immunotherapy in *Burkholderia cepacia* infection" *FEMS Immunology and Medical Microbiology* 10 (1995) 157-164.

Dinh et al., "A Family of Extracytoplasmic Proteins that Allow Transport of Large Molecules across the Outer Membranes of Gram-Negative Bacteria" *Journal of Bacteriology* 176:13 (Jul. 1994) 3825-3831.

Lomovskaya et al., "emr, an *Escherichia coli* locus for multidrug resistance" *Proc. Natl. Acad. Sci. USA* 89 (Oct. 1992) 8938-8942.

Rouch et al., "Efflux-mediated antiseptic resistance gene qacA from *Staphylococcus aureus*: common ancestry with tetracycline- and sugar-transport proteins" *Molecular Microbiology* 4:12 (1990) 2051-2062.

Saier et al., "Two novel families of bacterial membrane proteins concerned with nodulation, cell division and transport" *Molecular Microbiology* 11:5 (1994) 841-847.

Higgins, Christopher, "ABC Transporters: From Microorganisms to Man" *Annu. Rev. Cell Biol.* 8 (1992) 67-113.

DeShazer et al., "Molecular Characterization of Genetic Loci Required for Secretion of Exoproducts in *Burkholderia pseudomallei*" Journal of Bacteriology 181:15 (Aug. 1999) 4661-4664.

Cohn et al., "Verapamil-Tobramycin Synergy in *Pseudomonas cepacia* but Not *Pseudomonas aeruginosa* in vitro" Chemotherapy 41 (1995) 330-333.

Hancock, Robert, "Resistance Mechanisms in *Pseudomonas aeruginosa* and Other Nonfermentative Gram-Negative Bacteria" *Clin Infect Dis.* 27 (Suppl I) (1998) S93-S99.

Neyfakh, Alexander, "The Multidrug Efflux Transporter of *Bacillus subtilis* is a Structural and Functional Homolog of the Staphylococcus NorA Protein" *Antimicrobial Agents and Chemotherapy* 36:2 (Feb. 1992) 481-485.

* cited by examiner

*Primary Examiner*—Mark Navarro
(74) *Attorney, Agent, or Firm*—Mayer, Brown, Rowe & Maw LLP

(57) ABSTRACT

The present invention concerns antimicrobial compositions in particular compositions which affect *Burkholderia cepacia*, together with diagnostic test for same and uses of same.

13 Claims, No Drawings

SEQUENCE LISTING

<160> NUMBER OF SEQ ID NOS: 22

<210> SEQ ID NO 1
<211> LENGTH: 1554
<212> TYPE: DNA
<213> ORGANISM: Burkholderia cepacia
<220> FEATURE:
<221> NAME/KEY: CDS
<222> LOCATION: (1)..(1554)

<400> SEQUENCE: 1

```
atg tcc gcc acc acg gca tcc gcc gcg tcc cct gcc gcc gaa ccg gcg        48
Met Ser Ala Thr Thr Ala Ser Ala Ala Ser Pro Ala Ala Glu Pro Ala
  1               5                  10                  15 ccg ctg tcc ggc ggc gcc ctc gcg ctg ctc acc gtc ggg ctc gcg ctc        96
Pro Leu Ser Gly Gly Ala Leu Ala Leu Leu Thr Val Gly Leu Ala Leu
                 20                  25                  30 ggc acg ttc atg gaa gtg ctc gac acg tcg atc ggc gac gtc gcg gtg       144
Gly Thr Phe Met Glu Val Leu Asp Thr Ser Ile Gly Asp Val Ala Val
             35                  40                  45 ccg acg att ttg tgc agc ctc ggc gtc gcg acc agc gaa ggc acg tgg       192
Pro Thr Ile Leu Cys Ser Leu Gly Val Ala Thr Ser Glu Gly Thr Trp
         50                  55                  60 gtg att tcs tcg tat tcg gtc gcg tcc gcg atc gcg gtg ccg ctg acg       240
Val Ile Ser Ser Tyr Ser Val Ala Ser Ala Ile Ala Val Pro Leu Thr
 65                  70                  75                  80 ggc tgg ctt gcc cgg cgc gtc ggc gaa gtg cgg ctg ttc acc ctg tcg       288
Gly Trp Leu Ala Arg Arg Val Gly Glu Val Arg Leu Phe Thr Leu Ser
                 85                  90                  95 gtg ctc gcg ttc acg atc gcg tcg gcg ctc tgt ggc ctc gca ttg aac       336
Val Leu Ala Phe Thr Ile Ala Ser Ala Leu Cys Gly Leu Ala Leu Asn
                100                 105                 110 ttc gag acg ctg atc gcg ttt cgg ctg ctg cag ggc ctc gtg tcg ggg       384
Phe Glu Thr Leu Ile Ala Phe Arg Leu Leu Gln Gly Leu Val Ser Gly
            115                 120                 125 ccg atg gtg ccg ctg tcg cag acg atc ctg atg cgc agc tat ccg ccc       432
Pro Met Val Pro Leu Ser Gln Thr Ile Leu Met Arg Ser Tyr Pro Pro
        130                 135                 140 gcg aag cgc ggg ctc gcg ctc ggc tta tgg gcg atg acg gtg atc gtc       480
```

```
Ala Lys Arg Gly Leu Ala Leu Gly Leu Trp Ala Met Thr Val Ile Val
145                 150                 155                 160 gcg ccg atc ttc ggc ccg ctg ctc ggc ggc tgg atc agc gac aac tac      528
Ala Pro Ile Phe Gly Pro Leu Leu Gly Gly Trp Ile Ser Asp Asn Tyr
                165                 170                 175 acg tgg ccg tgg atc ttc tac atc aat ctg ccg atc ggg att ttc tcc      576
Thr Trp Pro Trp Ile Phe Tyr Ile Asn Leu Pro Ile Gly Ile Phe Ser
            180                 185                 190 gcg acc tgc gcg ttc ttc ctg ctg ggc cgc gag acg aag acg acg aaa      624
Ala Thr Cys Ala Phe Phe Leu Leu Gly Arg Glu Thr Lys Thr Thr Lys
        195                 200                 205 cag cgg atc gac gcg gtc ggg ctc acg ctg ctc gtg atc ggc gtg tcg      672
Gln Arg Ile Asp Ala Val Gly Leu Thr Leu Leu Val Ile Gly Val Ser
    210                 215                 220 tgc ctg cag atg atg ctc gac ctc ggc aag gac cgc gac tgg ttc agc      720
Cys Leu Gln Met Met Leu Asp Leu Gly Lys Asp Arg Asp Trp Phe Ser
225                 230                 235                 240 tcg tcg ttc atc gtt cgc gct cgc ctg atc gcg gtc gtg tcg ctc gcg      768
Ser Ser Phe Ile Val Arg Ala Arg Leu Ile Ala Val Val Ser Leu Ala
                245                 250                 255 ttc atg ctc gtc tgg gaa gcg acc gag aag gag ccg gtg gtc gac cta      816
Phe Met Leu Val Trp Glu Ala Thr Glu Lys Glu Pro Val Val Asp Leu
            260                 265                 270 cgc ctg ttc aag gat cgc aac ttt gct cgg cgc gct atc atc tcg ttc      864
Arg Leu Phe Lys Asp Arg Asn Phe Ala Arg Arg Ala Ile Ile Ser Phe
        275                 280                 285 ggc ttc atg gcg ttc ttc ggc tcg gtc gtg atc ttc ccg ctg tgg cag      912
Gly Phe Met Ala Phe Phe Gly Ser Val Val Ile Phe Pro Leu Trp Gln
    290                 295                 300 acc gtg atg ggc tac acg gcc ggc aag gca ctt ccg gcg acc gcg ccg      960
Thr Val Met Gly Tyr Thr Ala Gly Lys Ala Leu Pro Ala Thr Ala Pro
305                 310                 315                 320 gtt ggg ctg ctc gcg ctc gtg ctg tcg ccg ctg atc ggc cgc aac atg     1008
Val Gly Leu Leu Ala Leu Val Leu Ser Pro Leu Ile Gly Arg Asn Met
                325                 330                 335 cac cgg ctc gac ctg cgg atg gtc gcg agc ttc gcc ttt cat cgt gtt     1056
His Arg Leu Asp Leu Arg Met Val Ala Ser Phe Ala Phe His Arg Val
            340                 345                 350 tcg cga tcg tat cgg tta tgg aac tcg acg ttt acg ctc gac gtg ttt     1104
Ser Arg Ser Tyr Arg Leu Trp Asn Ser Thr Phe Thr Leu Asp Val Phe
        355                 360                 365 ttc aac cac gtg atc ctg ccg cgg ctc gtg cag ggg atc ggc gtc gcg     1152
Phe Asn His Val Ile Leu Pro Arg Leu Val Gln Gly Ile Gly Val Ala
    370                 375                 380 tgc ttc ttc gtg ccg atg acg acg atc acg ctg tcg agc atc ccc gac     1200
Cys Phe Phe Val Pro Met Thr Thr Ile Thr Leu Ser Ser Ile Pro Asp
385                 390                 395                 400 gag cgg ctg gcg agc gcc tcg ggc ctg tcg aac ttc ctg cgt acg ctg     1248
Glu Arg Leu Ala Ser Ala Ser Gly Leu Ser Asn Phe Leu Arg Thr Leu
                405                 410                 415 tcg ggc gcg atc ggc acc gcg gtc agc tcg acg ttc tgg gag aac gac     1296
Ser Gly Ala Ile Gly Thr Ala Val Ser Ser Thr Phe Trp Glu Asn Asp
            420                 425                 430 gcg atc tac cac cac gcg cgg ctc gcc gaa tcg gtg agc gtc tat gcg     1344
Ala Ile Tyr His His Ala Arg Leu Ala Glu Ser Val Ser Val Tyr Ala
        435                 440                 445 cag aac acg acc gac tat cag ggc gcg ctg gcg cag ctc ggc gtc gtg     1392
Gln Asn Thr Thr Asp Tyr Gln Gly Ala Leu Ala Gln Leu Gly Val Val
    450                 455                 460
```

```
ggc cag acc gcg aac gcg caa ctg aac cag atc gtc acg caa gca ggg    1440
Gly Gln Thr Ala Asn Ala Gln Leu Asn Gln Ile Val Thr Gln Ala Gly
465                 470                 475                 480 ctt cat gat ggc gac caa cga ctt ctt cac ctg tcg gcg atc gtg ttc    1488
Leu His Asp Gly Asp Gln Arg Leu Leu His Leu Ser Ala Ile Val Phe
                485                 490                 495 gtc gcg ctc gcg gcg ctc gtg tgg atc acg aag ccg aag aag ggc gcg    1536
Val Ala Leu Ala Ala Leu Val Trp Ile Thr Lys Pro Lys Lys Gly Ala
            500                 505                 510 ggg ccg gcg atg ggg cat                                            1554
Gly Pro Ala Met Gly His
            515
```

<210> SEQ ID NO 2
<211> LENGTH: 518
<212> TYPE: PRT
<213> ORGANISM: Burkholderia cepacia
<220> FEATURE:
<221> NAME/KEY: MOD_RES
<222> LOCATION: 67
<223> OTHER INFORMATION: Ser

<400> SEQUENCE: 2

```
Met Ser Ala Thr Thr Ala Ser Ala Ala Ser Pro Ala Ala Glu Pro Ala
 1               5                  10                  15

Pro Leu Ser Gly Gly Ala Leu Ala Leu Leu Thr Val Gly Leu Ala Leu
            20                  25                  30

Gly Thr Phe Met Glu Val Leu Asp Thr Ser Ile Gly Asp Val Ala Val
        35                  40                  45

Pro Thr Ile Leu Cys Ser Leu Gly Val Ala Thr Ser Glu Gly Thr Trp
    50                  55                  60

Val Ile Xaa Ser Tyr Ser Val Ala Ser Ala Ile Ala Val Pro Leu Thr
65                  70                  75                  80

Gly Trp Leu Ala Arg Arg Val Gly Glu Val Arg Leu Phe Thr Leu Ser
                85                  90                  95

Val Leu Ala Phe Thr Ile Ala Ser Ala Leu Cys Gly Leu Ala Leu Asn
            100                 105                 110

Phe Glu Thr Leu Ile Ala Phe Arg Leu Leu Gln Gly Leu Val Ser Gly
        115                 120                 125

Pro Met Val Pro Leu Ser Gln Thr Ile Leu Met Arg Ser Tyr Pro Pro
    130                 135                 140

Ala Lys Arg Gly Leu Ala Leu Gly Leu Trp Ala Met Thr Val Ile Val
145                 150                 155                 160

Ala Pro Ile Phe Gly Pro Leu Leu Gly Gly Trp Ile Ser Asp Asn Tyr
                165                 170                 175

Thr Trp Pro Trp Ile Phe Tyr Ile Asn Leu Pro Ile Gly Ile Phe Ser
            180                 185                 190

Ala Thr Cys Ala Phe Phe Leu Leu Gly Arg Glu Thr Lys Thr Thr Lys
        195                 200                 205

Gln Arg Ile Asp Ala Val Gly Leu Thr Leu Leu Val Ile Gly Val Ser
    210                 215                 220

Cys Leu Gln Met Met Leu Asp Leu Gly Lys Asp Arg Asp Trp Phe Ser
225                 230                 235                 240

Ser Ser Phe Ile Val Arg Ala Arg Leu Ile Ala Val Val Ser Leu Ala
                245                 250                 255

Phe Met Leu Val Trp Glu Ala Thr Glu Lys Glu Pro Val Val Asp Leu
            260                 265                 270
```

-continued

```
Arg Leu Phe Lys Asp Arg Asn Phe Ala Arg Arg Ala Ile Ile Ser Phe
            275                 280                 285
Gly Phe Met Ala Phe Phe Gly Ser Val Val Ile Phe Pro Leu Trp Gln
        290                 295                 300
Thr Val Met Gly Tyr Thr Ala Gly Lys Ala Leu Pro Ala Thr Ala Pro
305                 310                 315                 320
Val Gly Leu Leu Ala Leu Val Leu Ser Pro Leu Ile Gly Arg Asn Met
                325                 330                 335
His Arg Leu Asp Leu Arg Met Val Ala Ser Phe Ala Phe His Arg Val
            340                 345                 350
Ser Arg Ser Tyr Arg Leu Trp Asn Ser Thr Phe Thr Leu Asp Val Phe
        355                 360                 365
Phe Asn His Val Ile Leu Pro Arg Leu Val Gln Gly Ile Gly Val Ala
    370                 375                 380
Cys Phe Phe Val Pro Met Thr Thr Ile Thr Leu Ser Ser Ile Pro Asp
385                 390                 395                 400
Glu Arg Leu Ala Ser Ala Ser Gly Leu Ser Asn Phe Leu Arg Thr Leu
                405                 410                 415
Ser Gly Ala Ile Gly Thr Ala Val Ser Ser Thr Phe Trp Glu Asn Asp
            420                 425                 430
Ala Ile Tyr His His Ala Arg Leu Ala Glu Ser Val Ser Val Tyr Ala
        435                 440                 445
Gln Asn Thr Thr Asp Tyr Gln Gly Leu Ala Gln Leu Gly Val Val
    450                 455                 460
Gly Gln Thr Ala Asn Ala Gln Leu Asn Gln Ile Val Thr Gln Ala Gly
465                 470                 475                 480
Leu His Asp Gly Asp Gln Arg Leu Leu His Leu Ser Ala Ile Val Phe
                485                 490                 495
Val Ala Leu Ala Ala Leu Val Trp Ile Thr Lys Pro Lys Lys Gly Ala
            500                 505                 510
Gly Pro Ala Met Gly His
        515
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 3
cccgatcggc agattgatgt                                            20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 4
gacgtcgcgg tgccgacgat                                            20

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence: PCR primer

```
<400> SEQUENCE: 5
ttcacaggaa acag                                                    14

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: PCR primer

<400> SEQUENCE: 6
ttcacaggaa acag                                                    14

<210> SEQ ID NO 7
<211> LENGTH: 5
<212> TYPE: PRT
<213> ORGANISM: Burkholderia cepacia

<400> SEQUENCE: 7

Pro Leu Leu Gly Gly
  1               5

<210> SEQ ID NO 8
<211> LENGTH: 5
<212> TYPE: PRT
<213> ORGANISM: Burkholderia cepacia

<400> SEQUENCE: 8

Pro Leu Leu Arg Gly
  1               5

<210> SEQ ID NO 9
<211> LENGTH: 3
<212> TYPE: PRT
<213> ORGANISM: Burkholderia cepacia

<400> SEQUENCE: 9

Leu Asp Leu
  1

<210> SEQ ID NO 10
<211> LENGTH: 3
<212> TYPE: PRT
<213> ORGANISM: Burkholderia cepacia

<400> SEQUENCE: 10

Asp Leu Arg
  1

<210> SEQ ID NO 11
<211> LENGTH: 6
<212> TYPE: PRT
<213> ORGANISM: Burkholderia cepacia

<400> SEQUENCE: 11

Val Ile Ser Ser Tyr Ser
  1               5

<210> SEQ ID NO 12
<211> LENGTH: 7
<212> TYPE: PRT
<213> ORGANISM: Burkholderia cepacia

<400> SEQUENCE: 12
```

```
Ile Ser Phe Gly Phe Met Ala
  1               5
```

<210> SEQ ID NO 13
<211> LENGTH: 6
<212> TYPE: PRT
<213> ORGANISM: Burkholderia cepacia

<400> SEQUENCE: 13

```
Met Ala Phe Phe Gly Ser
  1               5
```

<210> SEQ ID NO 14
<211> LENGTH: 7
<212> TYPE: PRT
<213> ORGANISM: Burkholderia cepacia

<400> SEQUENCE: 14

```
Gln Thr Val Met Gly Tyr Thr
  1               5
```

<210> SEQ ID NO 15
<211> LENGTH: 7
<212> TYPE: PRT
<213> ORGANISM: Burkholderia cepacia

<400> SEQUENCE: 15

```
Leu Arg Met Val Ala Ser Phe
  1               5
```

<210> SEQ ID NO 16
<211> LENGTH: 7
<212> TYPE: PRT
<213> ORGANISM: Burkholderia cepacia

<400> SEQUENCE: 16

```
Phe Phe Val Pro Met Thr Thr
  1               5
```

<210> SEQ ID NO 17
<211> LENGTH: 7
<212> TYPE: PRT
<213> ORGANISM: Burkholderia cepacia

<400> SEQUENCE: 17

```
Leu Leu His Leu Ser Ala Ile
  1               5
```

<210> SEQ ID NO 18
<211> LENGTH: 15
<212> TYPE: PRT
<213> ORGANISM: Burkholderia cepacia

<400> SEQUENCE: 18

```
Ala Ile Ile Ser Phe Gly Phe Met Ala Phe Phe Gly Ser Val Val
  1               5                  10                  15
```

<210> SEQ ID NO 19
<211> LENGTH: 15
<212> TYPE: PRT
<213> ORGANISM: Burkholderia cepacia

<400> SEQUENCE: 19

```
Ser Val Val Ile Phe Pro Leu Trp Gln Thr Val Met Gly Tyr Thr
```

```
                1               5              10              15

<210> SEQ ID NO 20
<211> LENGTH: 15
<212> TYPE: PRT
<213> ORGANISM: Burkholderia cepacia

<400> SEQUENCE: 20

His Arg Leu Asp Leu Arg Met Val Ala Ser Phe Ala Phe His Arg
  1               5                  10                  15

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 21
cgacgtcgcg gtgccgacga t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 22
atgccccatc gccggccccg c                                              21
```

ANTIMICROBIAL COMPOSITIONS

CROSS REFERENCE TO RELATED APPLICATIONS

This application is a national phase application based on PCT/GB00/03 866, filed Oct. 9, 2000, and which further claims priority from British Application No. 9923858.6, filed Oct. 9, 1999. These applications in their entirety are incorporated herein by reference.

The present invention concerns antimicrobial compositions, in particular compositions which affect *Burkholderia cepacia*, together with diagnostic tests for same and uses of same.

*Burkholderia cepacia* is a major cause of soft rot in onions. Although rarely pathogenic in healthy individuals, it has emerged as an important opportunistic pathogen over the past 15 years being more commonly associated with pulmonary infections among individuals with Cystic Fibrosis (CF) and chronic granulomatus disease (Jarvis, W. R. et al., 1987, Eur. J. Epidemiol., 3: 233–36). CF patients become colonised with this bacterium from the environment and recent data has shown evidence of person-to-person transmission (Sajjan, U. S. et al., 1992, J. Clin. Invest., 89: 648–56; Govan, J. R. W. et al., 1993, Lancet, 342: 15–19). This has resulted in strict measures for segregating colonised individuals from non-colonised individuals in both hospital and social settings.

Colonisation of the respiratory tract with *B. cepacia* is associated with poor clinical prognosis: up to 20% of colonised individuals suffer from '*B. cepacia* syndrome', pneumonia associated with fever resulting in rapid and fatal clinical deterioration (Isles, A. et al., 1984, J. Pediatr., 104: 206–210; LiPuma, J. J. et al., 1990, Lancet, 336: 527–532).

*B. cepacia* has been shown to persist in the environment and it is resistant to disinfectants such as chlorhexidine (Sobel, J. D. et al., 1982, American J. Med., 73: 183–186). Treatment of patients colonised with this organism is problematic due to its intrinsic resistance to most clinically available antibiotics (Pitt, T. L. et al., 1996, J. Med. Microbiol., 44(3): 203–210). The resistance mechanisms of *B. cepacia* are fourfold. Firstly, selective permeability of the outer cell wall occurs, which may be due to changes in the lipopolysaccharide and pore forming outer membrane proteins (Nelson, J. W. et al., 1994, FEMS Immunol. Med. Micro., 8: 89–98). This type of mechanism in *B. cepacia* has been demonstrated to confer chloramphenicol resistance (Burns, J. L. et al., 1989, Antimicrob. Agents and Chemotherapy, 33: 136–141). Secondly, the intracellular targets of drugs may be altered so they are no longer rendered susceptible to the drug, for example, alteration in protein targets and decreased ribosomal susceptibility. Thirdly, inactivation of antibiotics, for example production of β-lactamases, including carbepenases which are capable of hydrolysing the most potent and broad-spectrum antibiotics (Simpson, I. N. et al., 1995, J. Antimicrob. Chemother., 32: 339–341). One of the main mechanisms of resistance in *B. cepacia* is believed to be active efflux via a drug-exclusion pump (Burns, J. L. et al., 1996, Antimicrob. Agents Chemother., 40(2): 307–313). However, this has not been proven and no drug efflux pumps have been identified. The existence of an ABC Transporter named hdrAB has previously been suggested (Journal of Antimicrobial Chemotherapy Volume 44, Supplement A, July 1999), but no sequence or indication of its identity was given.

A novel multi-drug efflux pump has now been identified in *B. cepacia*, a member of the major facilitator superfamily (Dinh, T. et al., 1994, J. Bacteriol., 176: 3825–3831, Marger, M. D. and Saier. M. H., 1993. Trends Biochem. Sci., 18: 13–20) i.e. not an ABC transporter protein (Higgins, C. F., 1992, Annu. Rev. Cell Biol., 8: 67–113) or member of the heavy metal resistance/cell division family (Saier, M. H. Jr. et al., 1994, Mol. Microbiol., 11: 1841–1847). It acts to pump out antibiotics and other molecules and thus helps provide the organism with its drug resistance. Inhibiting the pump hinders the efflux of e.g. antibiotics and allows them to affect (e.g. kill) the organism. Thus the pump and its inhibition provides a novel way to control *B. cepacia*. In particular it allows for the creation of a novel class of antimicrobial compositions as well as disinfectants.

Burnie et al. (1995. FEMS Immunology and Medical Microbiology, 10: 157–164) disclose a 28 kDa porin in *B. cepacia*. This is distinct from the multidrug efflux pump of the present invention which is a different type of protein and which has a predicted molecular weight of 49 kDa.

According to the present invention there is provided a multidrug efflux pump having the sequence of SEQ ID NO: 2 (referred to herein as bcrA) or a multidrug efflux pump having at least 85% homology therewith.

To determine the percent identity or homology between two amino acid or nucleic acid sequences, the sequences are aligned for optimal comparison purposes. Thus, for example, gaps can be introduced in one or both of the two sequences, and non-homologous (dissimilar) sequences can be disregarded for comparison purposes. In a preferred embodiment, the length of a first sequence aligned for comparison purposes is at least 30%, preferably at least 40%, more preferably at least 50%, even more preferably 60%, and even more preferably at least 70%, 80%, or 90% of the length of the second sequence in the region aligned. The amino acid residues or nucleotide at corresponding amino acid positions or nucleotide positions are then compared. When a position in the first sequence is occupied by the same amino acid residue or nucleotide residue as the corresponding position in the second sequence, then the molecules are identical at that position. The percent identity between the two sequences is a function of the number of identical positions shared by the sequences (taking into account where appropriate the number and length of gaps introduced to optimise the alignment). For polypeptide sequences, substitution of one amino acid for another with like characteristics can be made without affecting the structure or function of the polypeptide. Such conservative substitutions are likely to be phenotypically silent. Typically seen as conservative substitutions are the replacements, one for another, among the aliphatic amino acids Ala, Val, Leu and Ile, interchange of the hydroxyl residues Ser and Thr, exchange of the acidic residues Asp and Glu, substitution between the amino acid residues Asn and Gln, exchange of the basic residues Lys and Arg and replacements among the aromatic residues Phe, Tyr. Conservative amino acids substitutions which are likely to be phenotypically silent are described in Bowie et al., 1990. Science 247: 1306–1310. When aligning amino acid sequences, conservative amino acid substitutions can be taken into account to provide a score of the homology (also referred to as "similarity") between the sequences.

In a preferred embodiment, the comparison of sequences and determination of percent identity and/or percent homology may be determined using a mathematical algorithm (see, for example: Lesk, A. M. (ed.), 1988, Computational Molecular Biology, Oxford University Press, New York; Griffin, A. M. & Griffin, H. G. (eds), 1994, Computer Analysis of Sequence DATA, Humana Press, New Jersey;

von Heinje, G., 1987, Sequence Analysis in Molecular Biology, Academic Press, New York; and Gribskov, M. & Devereaux, J. (eds), 1991, Sequence Analysis Primer, M. Stockton Press, New York). Suitable algorithms for sequence alignment have been incorporated into the GCG software package (available at http://www.gcg.com). In addition, the nucleic acid or polypeptide sequences of the present invention may be used as a query sequence to perform a search against databases to, for example, identify other family members or related sequences. For example, such searches may be performed using the BLASTN (nucleic acid sequences) or BLASTP (amino acid sequences) programs (version 2.0—Altschul, S. F. et al., 1990, J. Mol. Biol. 2: 403–410; version 2.1-Altschul, S. F. et al., 1997, Nucleic Acids Research 25: 3389–3402). In a preferred embodiment, sequences are aligned, and identity and homology scores obtained, using the gapped Basic BLAST search (Version 2.1) with default searching and scoring parameters, available at the NCBI website (http://www.ncbi.nlm.nih.gov/BLAST/).

Searches performed on sequence databases have shown that the most similar known genes are the emrB gene from *E. coli* and the qacA gene from *Staphylococcus aureus* which are part of an operon that code for multidrug resistant extrusion pumps belonging to the MFS gene family (Lomovskaya, O. and Lewis, K., 1992, Proc. Natl. Acad. Sci., 89: 8938–8942; Rouch, D. A. et al., 1990, Mol. Microbiol., 4(12): 2051–2062). These two genes are 48.8% and 20.1% homologous respectively. A further unnamed gene has been identified in *Burkholderia pseudomallei* having 84.8% homology with the gene of the present invention. This protein (AF 110185) is disclosed in deShazer, D. et al. (1999, J. Bacteriology, 181(15): 46614664) as a "general secretory pathway" protein for the type II secretion pathway required for the secretion of protease, lipase and phospholipase C.

The homologues of the protein having SEQ ID NO: 2 may be those existing in other organisms or generated by modification of existing genes such as bcrA. For example homologues may have conserved substitutions, or they may have additions or deletions of amino acids. In particular the homologues may have at least 90% for example at least 95 or 99% homology with the sequence of SEQ ID NO: 2. The field of protein engineering is well known to one skilled in the art and such a person would be readily capable of modifying the protein of the present invention whilst retaining its functionality as a multidrug efflux pump. Homologues may be made by modifications which cause sequence differences, or which do not affect sequence, or both. Modifications may include chemical derivatisation of polypeptides, e.g. acetylation or carboxylation. Other modifications include glycosylation, for example during the polypeptides synthesis, processing or in further processing e.g. by enzymes (such as mammalian glycosylation enzymes) which affect glycosylation. Other modifications include phosphorylation of amino acids, e.g. phosphotyrosine, phosphoserine and phosphothreonine. Other modifications include the use of D-amino acids rather than the naturally occurring L-amino acids, and non-naturally occurring or synthetic amino acids such as β- or γ-amino acids.

Polypeptide fragment sequences within the multidrug efflux pump having the sequence of SEQ ID NO: 2 are also within the scope of the present invention. Such fragments may comprise amino acid sequences essential for functions of the multidrug efflux pump. Variants of the fragment sequences having the same function may have 10%, 20%, 50% or 100% amino acid homology with the corresponding fragment sequences within the multidrug efflux pump of SEQ ID NO: 2.

The multidrug efflux pump may be expressed by an organism of the *Burkholderia* or *Pseudomonas* genera. Experiments below show the protein to be expressed in *Burkholderia cepacia*, and the protein and its homologous multidrug efflux pumps can be expected to be expressed in a range of closely related organisms. In particular, *Burkholderia cepacia* used to be classified as *Pseudomonas cepacia* and due to the similarity of organisms of the *Burkholderia* and *Pseudomonas* genera the protein and its homologous multidrug efflux pumps are expected to be expressed in organisms of the genus *Pseudomonas*. Other genera of organisms expressing the protein and its homologous multi drug efflux pumps are *Klebsiella, Enterobacter, Serratia, Salmonella* and *Shigella*.

Also provided is a nucleotide sequence encoding a multidrug efflux pump according to the present invention. The nucleotide sequence may have the sequence of SEQ ID NO: 1. The present invention also extends to nucleotide sequences which encode the same protein but using different codons.

Also provided is a nucleic acid molecule which hybridises under moderate or high stringency conditions to a complement of the above-described nucleotide sequences. Hybridisation conditions are discussed in detail at pp 1.101–1.110 and 11.45–11.61 of Sambrook et al. (1989, Molecular Cloning, 2nd Edition, Cold Spring Harbor Laboratory Press). One example of hybridisation conditions that can be used involves using a pre-washing solution of 5×SSC, 0.5% SDS, 1.0 mM EDTA (pH 8.0) and attempting hybridisation overnight at 55° C. using 5×SSC. Hybridising nucleic acid sequences within the scope of the present invention include probes, primers or DNA fragments.

Also provided according to the present invention is a multidrug efflux pump according to the present invention for use in a method of treatment or diagnosis of the human or animal body. Such a first medical use has not previously been suggested or disclosed for the proteins of the present invention.

Also provided is the use of a multidrug efflux pump according to the present invention, or an immunogenic fragment thereof, in the manufacture of a medicament for the treatment of infection by an organism expressing same.

Since the drug efflux pump of the present invention is partially exposed on the exterior of the organism expressing it, it will display immunogenic epitopes. These epitopes may be readily determined using epitope mapping (Geysen, H. M et al., 1987, Journal of Immunological Methods, 102: 259–274; Geysen, H. M. et al., 1988, J. Mol. Recognit., 1(1):3241; Jung, G. and Beck-Sickinger, A. G., 1992, Angew. Chem. Int. Ed. Eng., 31:367–486). Once identified the epitopes (i.e. immunogenic fragments) may then be used in the formulation of a medicament. As well as using fragments of the pump displaying epitopes, mimotopes may be used which display the same epitope but which have a different sequence. These may be readily generated as described by Geysen (supra) using e.g. antibody specific against an epitope. Alternatively PCR may be used to synthesise immunogenic fragments (Gupta, S. et al., 1999, Biotechniques, 27(2): 328–332) to allow epitope mapping.

As can be seen from Table 2, 14 transmembrane helixes have been identified. Since they are not exposed on the exterior of the membrane they cannot display epitopes. Similarly, experiments (below) have shown that the first 46 amino acids of the protein do not display any epitopes.

Therefore, the immunogenic fragments may comprise sequence from other parts of the protein.

The present inventors have succeeded in identifying a number of epitopes which are displayed by the BcrA protein, and these form another aspect of the present invention. These epitopes are displayed by polypeptides having the sequences of SEQ ID NOs: 11–20. Thus according to the present invention there is provided a polypeptide having the sequence of any one of SEQ ID NOs: 11–20 and which displays an epitope. Reference herein to "immunogenic fragments" of the BcrA protein is considered to be reference to the polypeptides of SEQ ID NOs: 11–20.

For example the protein or immunogenic fragment of the present invention may be used in the manufacture of a vaccine. The protein or immunogenic fragments used in a vaccine includes immunogenic sequences homologous to the sequences of any one of SEQ ID NOs: 11–20 (ie. variants recognised by the same antibody) and heterologous sequences comprising immunogenic sequences (any one of SEQ ID NOs 11–20 and immunogenic sequences homologous thereto) fused to another sequence. The protein or immunogenic fragment may in particular be used in the manufacture of a vaccine for treatment of infections caused by organisms expressing same in Cystic Fibrosis patients. Also provided is a method of treating infections in a patient, particularly a Cystic Fibrosis patient, caused by organisms expressing the multidrug efflux pump of the present invention, comprising administering the multidrug efflux pump or an immunogenic fragment thereof to the patient. Such vaccines for administration to patients may be provided in a form additionally comprising a pharmaceutically acceptable carrier, diluent or excipient or for example an appropriate adjuvant. Such compounds will be readily apparent to one skilled in the art.

Medicaments according to the present invention may also comprise a suitable carrier, diluent or excipient (see for example Remington's Pharmaceutical Sciences and US Pharmacopeia, 1984, Mack Publishing Company, Easton, Pa., USA). The exact doses of medicament to be provided to a patient will be readily apparent to one skilled in the art and may be readily determined using a simple dose-response experiment.

Also provided is the use of an inhibitor of a multidrug efflux pump according to the present invention in the manufacture of a medicament for the treatment of infection by an organism expressing same. It may also be used together with at least one antibiotic, for example a tetracycline and/or quinolone. The quinolone antibiotic may be nalidixic acid. Administration to a patient of the medicament comprising an inhibitor of a multidrug efflux pump according to the present invention and the at least one antibiotic may be simultaneous or sequential. Also provided is a combined preparation of an inhibitor of a multidrug efflux pump according to the present invention and at least one antibiotic, for example a tetracycline and/or quinolone, for simultaneous, separate or sequential use in the treatment of infection by an organism expressing said multidrug efflux pump.

Also provided is the use of an inhibitor of a multidrug efflux pump according to the present invention in the manufacture of a disinfectant for an organism expressing same. It may also be used together with at least one quarternary ammonium disinfectant, for example chlorhexidine. As discussed above, *B. cepacia* and other organisms expressing multidrug efflux pumps according to the present invention can be persistent in the environment. Previously reported experiments have shown that e.g. *Burkholderia* and *Pseudomonas* can survive in disinfectant solutions, being resistant to e.g. quartemary ammonium compounds. Thus the present invention is not limited to the treatment of infection by such organisms, but also extends to disinfectants effective against same. In particular, such a disinfectant effective against an organism expressing a multidrug efflux pump according to the present invention may comprise an inhibitor of a multidrug efflux pump according to the present invention together with a quarternary ammonium disinfectant compound.

One particular advantage provided by the present invention is that by inhibiting the multidrug efflux pump it enables existing antibiotics and disinfectants which are otherwise ineffective or of limited effect against organisms expressing the efflux pump to become effective or have enhanced efficacy against the organisms. Thus a relatively simple modification to existing antimicrobial and disinfectant compositions can make them effective or enhance their efficacy against organisms expressing the efflux pump.

Thus also provided according to the present invention is antimicrobial composition comprising an inhibitor of a multidrug efflux pump according to the present invention and at least one antibiotic. Also provided is a method of treatment of infection of a patient by an organism expressing a multidrug efflux pump according to the present invention comprising administering to the patient such an antimicrobial composition. The class of antibiotics is a broad one but in combination with an inhibitor of a multidrug efflux pump of the present invention does display a general tendency to inhibit (i.e. hinder growth or reproduction or kill) microorganisms expressing said multidrug efflux pump. In particular, members of the classes of tetracyclines (for example, tetracycline) and quinolones (for example, nalidixic acid) are particularly effective. Also provided is a kit comprising an inhibitor of a multidrug efflux pump according the present invention and at least one antibiotic. The kit may be used in the treatment of infection of a patient by an organism expressing a multidrug efflux pump according to the present invention.

Also provided is an antimicrobial composition comprising an inhibitor of a multidrug efflux pump according to the present invention and at least one disinfectant, for example a quarternary ammonium disinfectant. Also provided is a method of disinfection comprising applying to an item (for example a surface) to be disinfected such an antimicrobial composition.

Inhibitors used in the present invention may include anything which is effective in inhibiting the efflux of drugs via the multidrug pump of the present invention. For example, an inhibitor may covalently bind to the efflux pump and prevent the passage of drugs. Alternatively, an inhibitor may act to prevent or down-regulate the synthesis of the pump at e.g. the transcriptional, translational or post-translational levels. Inhibitors may include antisense RNA. In particular inhibitors include antibodies and antigen binding fragments thereof specific against the efflux pump. The manufacture, synthesis and use of antibodies and antigen binding fragments thereof will be readily apparent to one skilled in the art (Harlow, E. and Lane, D., "Using Antibodies: A Laboratory Manual", Cold Spring Harbor Laboratory Press, New York, 1998). The antibody or antigenic fragment may be specific against any of the epitopes of the present invention i.e. any of SEQ ID NOs: 11–20.

Also provided according to the present invention is a method of detecting multidrug resistance in a bacterium comprising the steps of:

i) determining the presence of a multidrug efflux pump or nucleotide sequence encoding same according to the present invention in the bacterium; and ii) correlating the results of step (i) with the presence or absence of multidrug resistance in the bacterium.

The presence of a multidrug efflux pump may be determined by contacting the bacterium with a binding agent specific to the multidrug efflux pump and detecting and binding agent-multidrug efflux pump binding reaction. A binding agent may for example comprise an antibody or antigen binding fragment thereof specific against the multidrug efflux pump. Alternatively, it may comprise any other moiety which is capable of binding specifically to the pump.

The presence of a nucleotide sequence encoding a multidrug efflux pump may be determined by contacting the bacterium with a nucleotide sequence hybridising to the nucleotide sequence encoding the multidrug efflux pump or a transcription product thereof and detecting a nucleotide sequence-nucleotide sequence hybridising reaction. Also, the presence of a nucleotide sequence encoding a multidrug efflux pump may be determined by contacting the bacterium with a nucleotide sequence complementary to the nucleotide sequence encoding the multidrug efflux pump or a transcription product thereof and detecting a nucleotide sequence-nucleotide sequence binding reaction. Thus the presence of the gene encoding the multidrug efflux pump may be detected. This may, however, require a sample being tested to contain a relatively large number of bacteria in order to produce detectable results. Alternatively, mRNA could be detected—if the gene encoding the pump is being transcribed (which will be necessary to effect drug resistance in the bacterium) then mRNA should be detectable and should be present in greater quantities than the nucleotide sequence encoding the pump.

Also provided is a method of detecting the presence of a bacterium having multidrug resistance conferred by the presence of a multidrug efflux pump according to the present invention, comprising:

i) taking a sample from a patient;

ii) determining the presence in the sample of a multidrug efflux pump or nucleotide sequence encoding same according to the present invention; and iii) correlating the results of step (ii) with the presence or absence of a bacterium having multidrug resistance.

The presence of a multidrug efflux pump may be determined by contacting the sample with a binding agent specific to the multidrug efflux pump and detecting and binding agent-multidrug efflux pump binding reaction. The binding agent may for example comprise an antibody or antigen binding fragment thereof specific against the multidrug efflux pump, for example specific against any of the epitopes of the present invention. The presence of a nucleotide sequence encoding a multidrug efflux pump may be determined by contacting the bacterium with a nucleotide sequence hybridising to the nucleotide sequence encoding the multidrug efflux pump or a transcription product thereof and detecting a nucleotide sequence-nucleotide sequence hybridising reaction. Also, the presence of a nucleotide sequence encoding a multidrug efflux pump may be determined by contacting the bacterium with a nucleotide sequence complementary to the nucleotide sequence encoding the multidrug efflux pump or a transcription product thereof and detecting a nucleotide sequence-nucleotide sequence binding reaction.

Patient samples used in any such methods may comprise for example blood, serum, bronchial aspirates or sputum.

Also provided according to the present invention is a method of treatment of infection of a patient by an organism expressing a multidrug efflux pump according to the present invention, comprising administering to the patient an antimicrobial composition according to the present invention, i.e. comprising an inhibitor of a multidrug efflux pump according to the present invention and at least one antibiotic.

Such methods of treatment are particularly useful for Cystic Fibrosis sufferers who are particularly prone to infection by multidrug resistant organisms, and thus the patient may be a Cystic Fibrosis sufferer.

Also provided according to the present invention is a polypeptide having the sequence of any one of SEQ ID NOs: 11–20 and which displays an epitope. Also provided is immunogenic sequences homologous to the sequences of any one of SEQ ID NOs: 11–20 which display an epitope (ie. variants recognised by the same antibody) and heterologous sequences comprising immunogenic sequences (any one of SEQ ID NOs 11–20 which display an epitope and immunogenic sequences homologous thereto) fused to another sequence.

Also provided according is a method for conferring antibiotic resistance to an organism comprising introducing a multidrug efflux pump according to the present invention into said organism. Also provided is an organism into which a multidrug efflux pump according to the present invention has been introduced.

Further provided according to the present invention is a data carrier comprising the sequence of a molecule according to any one of SEQ ID NOs 1–4,7–22. The data carrier may be a machine readable data carrier, for example a computer disk or CD.

Also provided is a method of analysing a sequence according to any one of SEQ ID NOs 1–4,7–22, said method comprising one or more of the following: determining the degree of sequence identity of homology of said sequence with another sequence, determining the secondary structure of the sequence, determining the molecular weight of the structure, and determining the immunological and chemical characteristics of the sequence. Methods for analysing nucleic acid and protein sequences of the present invention include those known in the art, for example as described in: Lesk, A. M. (ed.), 1988 (supra); Griffin, A. M. & Griffin, H. G. (eds), 1994 (supra); von Heinje, G., 1987 (supra); and Gribskov, M. & Devereaux, J. (eds), 1991 (supra).

Also provided is a database incorporating any one of SEQ ID NOs 1–4,7–22. Further provided is a computer set up to analyse any one of SEQ ID NOs 1–4,7–22.

The invention will be further apparent from the following description which shows by way of example only one form of multidrug efflux pump.

EXPERIMENTAL

Materials and Methods

Bacterial Strains from Plasmids

B. cepacia J23 15 Edinburgh was obtained from a patient with Cystic Fibrosis. Sera were obtained from infected patients with Cystic Fibrosis with repeated positive sputum culture for B. cepacia. Microbial culture and biochemical identification was carried out to confirm identity.

DNA Isolation and Lambda ZAPII Library Preparation

DNA was isolated and restricted according to Goldbang, N. et al. (1996, J. Clin. Pathol., 42: 861–863) to produce a partial digest with the enzyme Sau 3a. A lambda ZAPII library was prepared with an insert size range of 3–5 kb according to protocols from Clontech Laboratories Inc., Cambridge. England.

Antibody Screening

Sera was taken from a patient with chest infection due to *B. cepacia* and used for antibody screening. *Escherichia coli* XL 1—Blue cells were infected with the lambda ZAPII phage on L broth agar (bacto-tryptone 10 g/L, yeast extract 5 g/L, NaCl 10 g/L, maltose 2 g/L, bacto-agar 15 g/L) at c. 3000 pfu/85 mm plate. This was incubated at 42° C. for 3 hours. Plaques were transferred to nitrocellulose filters (0.45 µm pore size; Sartorius AG, Goettingen, Germany), impregnated with 10 mM isopropyl β-D thio-galactopyranoside (IPTG), at 37° C. for 2 hours. These filters were blocked overnight at 4° C. with bovine serum albumin (BSA; Sigma) 3% in buffered saline (150 mM NaCl, 10 mM Tris). Serum diluted 100-fold in BSA 3%, was added to the filters and incubated at room temperature for 2 hours, the filters were washed for 30 minutes in washing solution (150 mM NaCl, Tween 20 0–05%), before the second antibody, anti-human IgG conjugated to alkaline phosphatase (Sigma) diluted 1000-fold in BSA 3%, was added. After 1 hour at room temperature, the filters were again washed and stained with equal volumes of naphthol ASMX phosphate (0.4 mg/ml in distilled water; Sigma) and Fast Red TR salt (6 mg/1 in 0.2 M Tris pH 8.2; Sigma) (the Fast Red Stain). Positive plaques were transferred to 1.5-ml tubes containing 200 µl of SM (100 mM NaCl, 50 mM Tris-HCl, pH 7.5, 10 mM $MgSO_4$, gelatin 0.001%), and two-to-three drops of chloroform. Plaque purification was performed by repeating the above. This lead to the identification of a positive plaque which was subsequently sequences and this produced an open reading frame starting at amino acid 46 and continuing to the carboxy end of the protein.

Searching the database revealed that this was not a full sequence so that further cloning was required to identify the full amino acid end of the molecule. For this purpose a digoxigenin labelled probe was made by the polymerase chain reaction so that the library could be rescreened. The primers for this were EMRC (SEQ ID NO: 4) amino end and EMRN (SEQ ID NO: 3) carboxy end.

Synthesis of Polymerase Chain Reaction (PCR) Derived Digoxigenin Labelled Probe:

2 µl aliquots purified pMKC plasmid DNA were used for the PCR, in a final reaction volume of 100 µl in 10 nM Tris-HCl (pH 8.8) 50 mM KCl, 1.5 mM $MgCl_2$ (Perkin Elmer) containing 100 pmol/µl each of primers EMRC and EMRN (see Table 1), 200 µM of each digoxigenin-11-uridine-5'-phosphate labelled dNTPs (Boehringer Mannheim) and 5 U Taq DNA polymerase (Perkin Elmer). The reaction mix was subjected to an initial denaturation at 94° C. for 5 minutes and PCR was done on a GeneAmp 9600 thermal cycler (Roche Diagnostic Systems) as follows: 94° C. for 1 minute, 55° C. for 30 seconds, and 72° C. for 1 minute. After completion of 30 cycles, the reaction was held at 72° C. for 7 minutes and were then cooled to 4° C. Control tubes with no template DNA were included.

Amplified products were resolved by gel electrophoresis in 100 ml 1.0% (w/v) agarose gel in 1×Tris-acetate (TAE) buffer, containing 0.5 µg/ml ethidium bromide. Molecular markers (the EcoRI/HindIII digested DNA of Goldbang, N. et al., 1996, supra) were included and the PCR products resolved by electrophoresis at 80V for 1 hour.

Media and Reagents

NZY Broth (Per Liter):

5 g NaCl, 2 g $MgSO_4.7H_2O$, 5 g yeast extract and 10 g NZ amine (casein hydolysate) was added to deionised water to a final volume of 1 liter. The pH was adjusted to 7.5 with NaOH and sterilised by autoclaving at 15 lb./sq.in. for 15 minutes.

NZYagar (Per Liter):

5 g NaCl, 2 g $MgSO_4.7H_2O$, 5 g yeast extract, 10 g NZ amine (casein hydolysate) and 15 g agar was added to deionised water to a final volume of 1 liter. The pH was adjusted to 7.5 with NaOH and sterilised by autoclaving at 15 lb./sq.in. for 15 minutes. The agar was allowed to cool and then poured into petri dishes.

NYZ Top Agar (Per Liter):

To 1 liter of NZY broth 0.7% (w/v) agarose was added and sterilised by autoclaving at 15 lb./sq.in. for 15 minutes. Before it was used the top agar was melted and cooled to 48° C.

LB-Kanamycin Agar (Per Liter):

10 g NaCl, 10 g tryptone, 5 g yeast extract and 20 g agar was added to deionised water to a final volume of 1 liter. The pH was adjusted to 7.5 with NaOH and sterilised by autoclaving at 15 lb./sq.in. for 15 minutes. The agar was allowed to cool to 55° C. before addition of 50 mg filter sterilised kanamycin and then poured into petri dishes.

20×SSC (Per Liter):

175.3 g NaCl and 88.2 g of sodium citrate were dissolved in 800 ml deionised water. The pH was adjusted to 7.0 using NaOH, and the volume made up to 1 liter with deionised water and then sterilised by autoclaving at 15 lb./sq.in. for 15 minutes.

50×Tris-Acetate Buffer (TAE):

242 g tris base was added to 57.1 ml glacial acetic acid and 100 ml 0.5M EDTA (pH 8.0) and the reminder of the volume made up to 1 liter with deionised water and then sterilised by autoclaving at 15 lb./sq.in. for 15 minutes.

Sodium Acetate-pH 5.2:

4.08 g $NaC_2H_3O.3H_2O$ was dissolved in 8 ml distilled water and the pH adjusted to 5.2 with dilute acetic acid, the volume was made up to 10 ml and the solution sterilised by autoclaving at 15 lb./sq.in. for 15 minutes.

Screening of the *b. cepacia* Genomic Library

Preparation of Plating Cultures:

NZ amine and yeast extract (NZY) broth, supplemented with 0.2% (w/v) maltose and 10 mM $MgSO_4$, was inoculated with a single *E. coli* XL 1-Blue MRF colony and grown overnight at 37° C. The bacterial culture was harvested by centrifugation at 4500×g for 15 minutes and the pellet resuspended in ice-cold 10 mM $MgSO_4$ to an optical density (OD) (600 nm) of 0.5. 200 µl of the resuspended bacterial culture was added to $10^{-2}$ diluted bacteriophage library and incubated at 37° C. for 15 minutes. 3 ml NZY top agar (48° C.) was added and the infected cells poured onto an NZY agar plate and incubated overnight at 37° C.

Overlaying the Nylon Membranes:

Each agar plate, containing plaques, was overlaid with a nylon membrane for 2 minutes. The membrane was denatured in 1.5M NaCl, 0.5M NaOH for 2 minutes and then neutralized in 1.5M NaCl, 0.5M Tris-HCl (pH 8.0) for 5 minutes before being rinsed briefly in 0.2M Tris-HCl (pH 7.5) 2×saline sodium citrate (SSC) buffer solution. The membrane was blotted briefly on Whatman (RTM) 3MM paper and the DNA cross-linked to the membrane using the Stratalinker (RTM) UV crosslinker set at 120.000 μJ UV energy for 30 seconds. The agar plates of the transfer were stored at 4° C.

Hebridisation of the Nylon Membranes:

The nylon membranes were pre-hybridised at 68° C. in hybridisation buffer (5×SSC. 1% (w/v) blocking reagent (added from 10% sterile blocking solution), 0.1% (w/v) N-lauroylsarcosine, 0.02% (w/v) sodium dodecyl sulphate (SDS)). After 2 hours the hybridisation buffer was replaced with fresh hybridisation buffer containing digoxigenin-labelled probe at a final concentration of 500 ng/ml and incubated overnight at 68° C. The filters were washed 2×5 minutes in 2×SSC, 0.1% SDS at room temperature and then 2×15 minutes in 0.1×SSC. 0.1% SDS at 68° C.

Immunological Detection:

Positive clones were identified using the DIG DNA Detection Kit (Boehringer Mannheim). The membrane was washed briefly in washing buffer (0.1M maleic acid, 0.15M NaCl (pH 7.5)) containing 0.3% (w/v) tween 20 before incubation for 30 minutes in 100 ml blocking solution (0.1M maleic acid, 0.15M NaCl (pH 7.5) containing blocking reagent to a final concentration of 1% (w/v)). The membrane was transferred to 150 mU/ml anti-digoxigenin-AP conjugate in 20 ml blocking solution and incubated for 30 minutes. Any unbound antibody-conjugate was removed by washing 2×15 minutes in 100 ml washing buffer (0.1M maleic acid. 0.15M NaCl (pH 7.5)). The membrane was equilibrated for 2 minutes in buffer containing 100 mM Tris-HCl, 100 mM NaCl, 50 mM $MgCl_2$ (pH 9.5) before incubation with 10 ml colour substrate solution (200 μl NBT/NCIP stock solution (Boehringer Mannheim) to 10 ml 100 mM Tris-HCl, 100 mM NaCl, 50 mM $MgCl_2$ (pH 9.5) in the dark. After overnight incubation the reaction was stopped by washing the membrane in 50 ml buffer containing 100 mM Tris-HCl, 1 mM EDTA (pH 8.0). All steps, except the colour reaction, were carried out with shaking. Positive isolates were further purified by secondary and tertiary screening.

Single-Clone Excision of the ZAP Express Vector:

(i) Preparation of the Excised pBK-CMV Phagemid Vector

Separate overnight cultures of *E. coli* XL I-Blue MRF, supplemented with 0.2% (w/v) maltose, and *E. coli* XLOLR in NZY broth were grown at 37° C. The bacterial cultures were harvested by centrifugation at 4500×g for 15 minutes and resuspended in ice-cold 10 mM $MgSO_4$ to an OD (600 nm) of 1.0. In a Falcon 2059 polypropylene tube the following were added: 200 μl *E. coli* XL1-Blue MRF at an OD (600 nm) of 1.0, 250 μl phage stock (>1×$10^5$ phage particles) and 1 μl of ExAssist helper phage (>1×$1^60$ pfu/ml) and incubated at 37° C. for 15 minutes. 3 ml NZY both was added and the reaction mix incubated at 37° C. for 3 hours, with shaking. The reaction mix was heated to 65–70° C. for 20 minutes followed by centrifugation at 4500×g for 15 minutes. The supernatant (which contained the excised pBK-CMV phagemid vector packaged as filamentous phage particles) was decanted into a fresh Falcon 2059 polypropylene tube and stored at 4° C.

(ii) Plating of the Excised Phagemid Vectors

200 μl freshly grown XLOLR cells at an OD (600 nm) of 1.0 were added to 10 μl and 100 μl of the phage supernatant and incubated at 37° C. for 15 minutes. 300 μl NZY broth was added and the reaction mix incubated for a further 45 minutes. 200 μl of the cell mixture from each reaction mix was plated onto LB-Kanamycin agar plates (50 μg/ml) and incubated overnight at 37° C. The plates were stored at 4° C. and glycerol stocks of a single purified colony made and stored at −80° C.

(iii) Wizard (RTM) Plus SV Midiprep DNA Purification

Plasmid DNA, containing the DNA insert, was purified using Wizard (RTM) Plus SV Midiprep DNA Purification Kit (Promega). 50 ml NZY broth, supplemented with 100 g/ml ampicillin, was inoculated with a single *E. coli* colony (containing the pBK-CMV plasmid and insert) and grown overnight at 37° C. The bacterial culture was harvested by centrifuged at 4500×g for 15 minutes and the pellet resuspended in 3 ml Wizard (RTM) Plus SV midiprep cell resuspension solution. The cells were lysed by addition of 3 ml Wizard (RTM) Plus SV midiprep cell lysis solution. The lysate was left on ice for 30 minutes before shaking vigorously and then centrifuged at 14000×g for 30 minutes at 4° C. The cleared lysate was added to 10 ml Wizard (RTM) Plus SV midiprep 30° C. resuspension resin and transferred to a Wizard (RTM) Plus SV midiprep midicolumn. A vacuum was applied to pull the resin/DNA into the midicolumn and the column washed 2×in 15 ml Wizard (RTM) Plus SV midiprep column wash solution and dried for 30 seconds. The midicolumn was transferred to a 1.5 ml eppendorf and centrifuged at 10000×g in a microcentrifuge for 2 minutes to remove any residual column wash solution. Plasmid DNA was eluted with 300 μl 65–70° C. nuclease free water by centrifugation at 10000×g for 20 seconds. Any fine resins were removed by centrifugation at 10000×g for 5 minutes.

The DNA concentration was calculated using the Gene Quant (Pharmacia Biotech) and purity checked by gel electrophoresis on a 1% (w/v) agarose gel in 1×TEA stained with 0.5 μg/ml ethidium bromide.

ABI DNA Sequencing:

50 ng/kb plasmid DNA and insert, in a final reaction volume of 10 μl, was added to 1.6 pmol appropriate primer (see Table 1) and 4 μl d-Rhodamine big-dye terminator mix (Applied Biotechnologies). The reaction mix was subjected to an initial denaturation at 96° C. for 4 min and then partially amplified on a GeneAmp 9600 thermal cycler (Roche Diagnostic Systems) as follows: 96° C. for 30 seconds, 50° C. for 15 seconds, 60° C. for 4 minutes. After completion of 25 cycles the reaction mix was made up to 100 μl with nuclease free water. The DNA was precipitated by addition of 2.5 volumes ice-cold 95% ethanol and 3 μl 3M sodium acetate (pH 5.2) and incubated at room temperature for 30 minutes. The reaction mix was centrifuged at 18000×g for 15 minutes, the supernatant removed and 250 μl ice-cold 70% ethanol added to the DNA pellet and incubated at room temperature for 30 minutes. The reaction mix was centrifuged at 18000×g for 15 minutes the supernatant removed and the pellet dried by exposure to air. The DNA was sequenced on an ABI 377 Prism.

Epitope Mapping of the BcrA Protein

A series of overlapping nonapeptides covering the derived amino acid sequence of the BcrA protein (SEQ ID NO: 2) were synthesised on polyethylene pins with reagents from an epitope scanning kit (Cambridge Research Biochemicals, Cambridge, UK) as described by Geysen et al. (1987, Journal of Immunological Methods, 102:259–274). The peptides are then used as the basis of an ELISA (enzyme-linked immunosorbent assay) to detect specific antibodies in sera from CF patients infected with *B. cepacia*. The resulting ELISA absorbance values are used to determine where the epitopes are located.

Generation of Synthesis Schedules:

The 518 amino acid residues of the *B. cepacia* BcrA protein (SEQ ID NO: 2) were entered into the Chiron Development software program (Chiron technologies). From these sequences synthesis schedules were generated which allowed the BcrA protein to be represented as a series of sequential overlapping peptides, each nine amino acids in length. Each peptide differed from the preceding one by a single amino acid: i.e. peptide one consisted of amino acids 1 to 9; peptide two consisted of amino acids 2 to 10, etc. This continued until the entire length of the bcrA gene had been covered.

Synthesis of Peptides:

The peptides were synthesised onto polyethylene pins arranged in a standard microtitre format. Synthesis of the peptides was done according to the methodology from the Chiron Technologies non-cleavable peptide synthesis manual.

Amino-acids:

The amino acids used were active esters, which had their amino groups protected with the 9-fluoreonylmethoxycarbonyl (Fmoc) group (Sigma, Calbiochem). The peptides were synthesised at the rate of one amino acid per pin, per day.

Fmoc Deprotection and Washing:

Removal of the Fmoc protecting group was achieved in the following way: Blocks of polypropylene pins were immersed in a bath containing 20% piperidine in dimethylformamide (DMF) (BDH Chemicals Ltd.) for 20 min at room temperature. The blocks were removed and then washed in a DMF bath for 2 min. Excess DMF was flicked off and the pins immersed in a methanol (BDH Chemicals Ltd.) bath for 2 min. This washing step was repeated three times, each time using a fresh methanol bath. The blocks were allowed to air dry in an acid-free fume cupboard for 30 min.

Preparation of Amino-Acids for Coupling:

The amino acids were weighed to give a final concentration of 100 mM and dissolved in a volume of 1-hydroxybenzotriazole (HOBT) (Sigma Chemical Co.) in DMF as specified by the schedule.

Coupling Reaction:

100 µl of the Fmoc amino-acid esters were dispensed into the wells of polypropylene microtitre plates as specified by the schedule. The blocks of deprotected pins were placed into the wells, sealed in a clean plastic bag and left overnight at room temperature.

Processing the Blocks after Coupling:

The blocks of pins were removed from the amino acid solutions and placed in a methanol bath for 5 min at room temperature, with agitation. After being left to air dry for 2 min, the blocks were placed in a DMF bath for 5 min.

The deprotection, washing, coupling and washing steps continued until all the amino acids were coupled and all the peptides synthesised onto the pins.

Side-Chain Deprotection:

All the protecting groups to protect the side-chain functions were removed by placing the blocks of pins into a mixture of trifluroacetic acid, anisole and ethanedithiol (Sigma Chemical Co.) (19:1:1 v/v) for 3 h at room temperature. The blocks were then fully immersed in methanol for 10 min and then soaked in 0.5% glacial acetic acid (BDH Chemicals Ltd.) in methanol/water (1:1 v/v) for 1 h. The blocks were immersed twice more in methanol baths for 2 min and then allowed to air dry overnight in an acid free fume cupboard.

Collection of Sera from CF Patients:

A total of 17 sera, one from each of 17 CF patients, were collected at the Cystic Fibrosis Unit in Wythenshawe Hospital, Manchester, UK. Group 1 sera (n=5) were collected from CF patients infected with *Pseudomonas aeruginosa* and *Burkholderia cepacia*, Group 2 sera (n=4) were collected from CF patients infected with *P. aeruginosa*, Group 3 sera (n=2) were collected from CF patients with no indication of infection with either *P. aeruginosaor B. cepacia*, Group 4A sera (n=4) were collected from CF patients infected with *B. cepacia* but who were well, and Group 4B sera (n=2) were collected from CF patients infected with *B. cepacia* who were unwell and hospitalised.

ELISA Testing:

Blocking step: 150 µl of 3% bovine serum albumin (BSA), (Sigma Chemical Co.) in phosphate buffered saline (PBS), was dispensed into each well of a Falcon 3912 Microtitre Plate. The blocks of pins were placed into the wells and left for 1 h at room temperature on a shaking platform at 100 rpm.

Addition of test serum: 150 µl of a 1 in 500 dilution of the test serum in 3% BSA in PBS was dispensed into microtitre plates. The pins were placed into the wells and incubated overnight at 4° C.

Wash step: Following incubation the pins were washed 4×10 min in a 0.01M PBS (pH 7.2) bath. Between washes the pins were shaken and blotted to remove excess washing solution.

Addition of immunoglobulin G (IgG): After washing, the pins were placed into microtitre plates containing 100 µl horseradish peroxidase conjugated goat anti-human immunoglobulin G (IgG) (Sigma Chemical Co.) diluted 1 in 2000 in 3% BSA in PBS. The pins were incubated for 1 h at room temperature on a shaking platform at 100 rpm. Wash step: Prior to the substrate reaction, the pins were washed 4×10 min in a 0.01 M PBS (pH 7.2) bath. Between washes the pins were shaken and blotted to remove excess washing solution.

Substrate reaction: 0.5 mg/ml 2,2'Azino-bis(3-Ethylbenzthiazoline-6-Sulphonic Acid) (ABTS) (Sigma Chemical Co.) was dissolved in 100 ml of citrate buffer (pH 4.0). To this buffer 0.01% (v/v) hydrogen peroxide (Sigma Chemical Co.) was added. 150 µl was dispensed into microtitre plates. The pins were placed into the wells and left at room temperature for 30 min on a shaking platform at 100 rpm. Removing the pins from the wells stopped the reaction. The microtitre plates were read using a Titertek Multiskan® Plus Microplate Reader at a wavelength of 405 nm.

Removal of Antibody from Pins:

Bound antibody was removed from the pins by sonification in a Decon Ultrasonic Bath (Decon Laboratories) containing a solution of 0.01 M PBS/1% (w/v) SDS and 0.1% (w/v) urea (Sigma Chemical Co.) for 20 min at 60° C. Following sonification the pins were washed 2×30 sec in water heated to 60° C. followed by a further wash in water (60° C.) for 1 h. The pins were placed in a bath containing boiling methanol for 30 sec and then allowed to air dry for a minimum of 30 min. The pins were then ready for testing the next serum.

Collection of Absorbance Data:

After all the sera had been tested, the absorbance values at 405 nm for each peptide was collated and the amino acid sequence of the epitopes ascertained. Epitopes were determined by analysis of the values for Group 3 and Group 4, and in comparison with the other Groups. Peptides were defined as a run of peptides (of three or more amino acid residues) with absorbance value differences between Group 4A and Group 3 of greater than 0.8.

Results of the epitope mapping (Table 3) identified seven epitopes displayed by the protein, having SEQ ID NOs: 11–17. Another four putative epitopes displayed by the protein have SEQ ID NOs: 7–10.

Preparation of Phage Antibody Display Library and scFv

The phage antibody display library and scFv were produced essentially as described previously (Burnie et al., 2000, Infection & Immunity 68: 3200–3209, which is incorporated herein by reference). Briefly, mRNA was prepared from 20 ml of patient peripheral blood by separation of lymphocytes over Ficoll followed by guanidinium thiocyanate extraction and purification of an oligo (dT)-cellulose column (Quick Prep mRNA; Pharmacia, St Albans, United Kingdom). First-strand cDNA synthesis was performed with a constant-region primer for all four subclasses of human IgG heavy chains (Hu1gG1 to 4) using avian myeloblastosis virus reverse transcriptase (HT Biotechnology, Cambridge, United Kingdom). The heavy-chain variable-domain genes were amplified by primary PCRs with family-based forward (HuJH1 to −6) and backforward (HuVH11a to 6a) primers (all abovementioned IgG primer sequences are provided in Marks, J. D. et al., 1991. J. Mol. Biol. 222: 581–597, which is incorporated herein by reference). An Sfi1 restriction site was introduced upstream to the VH3a back-generated product prior to assembly with a diverse pool of light-chain variable-domain genes. The latter also introduced a linker fragment ($Gly_4$ $Ser_3$) and a downstream Not1 site. By use of the Sfi1 and Not1 restriction enzyme sites, the product was unidirectionally cloned into a phagemid vector. The ligated vector was introduced into E. coli TG1 by electroporation, and phages were rescued with the helper phage M13K07 (Pharmacia).

Peptides for Panning:

To enrich for antigen-specific scFv, the phage library was panned against 15-mer peptides representing four of the epitopes delineated by epitope mapping: Peptide 1: AIISF-GFMAFFGSVV (SEQ ID NO: 18), incorporating Epitope 2 (SEQ ID NO: 12) and Epitope 3 (SEQ ID NO: 13); Peptide 2: SVVIFPLWQTVMGYT (SEQ ID NO: 19), incorporating Epitope 4 (SEQ ID NO: 14); and Peptide 3: HRLDRMVAS-FAFHR (SEQ ID NO: 20), incorporating Epitope 5 (SEQ ID NO: 15). Panning was performed in immunotubes coated with peptide (10 ng/ml) or the purified transporter (1 mg/ml). Bound phages were eluted with log-phase E. coli TG1. After rescue with M13K07, the phages were repanned against peptide a further three times. BstN1 (New England Biolabs, Hitchen, United Kingdom) DNA fingerprinting was used to confirm enrichment of specific scFv after successive rounds of panning.

Cloning of the bcrA into pBAD-TOPO

Before the antibiotic sensitivity tests were done the bcrA gene was cloned using pBAD-TOPO (Invitrogen) into TOP 10 E. coli.

Initial Amplification:

Amplification of bcrA gene was performed in a GeneAmp 9600 Thermal Cycler (Roche Diagnostic Systems) with PCR mixtures containing 1 µl purified BcrA plasmid DNA (approximately 1 µg DNA) in a final reaction volume of 25 µl in 10 mM Tris-HCl (pH 8.8), 50 mM KCl, 1.5 mM MgCl2 and containing 200 µM of each deoxynucleoside triphosphate, 25 pmol/µl each of BcrA forward primer (5' CGA CGT CGC GGT GCC GAC GAT—SEQ ID NO: 21) and BcrA reverse primer (5' ATG CCC CAT CGC CGG CCC CGC—SEQ ID NO: 22), and 5 U of Taq DNA polymerase (Boehringer Mannheim). Thermal cycling conditions were an initial denaturation of 5 min at 94° C. followed by 30 cycles of 1 min at 94° C. 1 min at 50° C., and 1 min at 72° C. Following amplification the samples were incubated at 72° C. and then held at 4° C. Amplified products were resolved by gel electrophoresis in 1% agarose in Tris acetate buffer, containing 0.5 µg/ml ethidium bromide. The band was cut out from the gel and melted by heating to 65° C. for 10 minutes.

Cloning of bcrA into pBAD-TOPO and Transformation into TOP10 E. coli:

3 µl fresh PCR product was added to 1 µl BAD-TOPO vector in a final reaction volume of 5 µl and incubated at room temperature for 5 min. 2 µl of the pBAD-TOPO cloning reaction was added to a vial of One Shot Chemically Competent TOP10 E. coli and incubated for 30 minutes. The cells were then heat shocked at 42° C. before incubation on ice for 2 minutes. After addition of 250 µl SOC medium the cells were incubated horizontally at 37° C. for 1 hour the transformation was spread onto a prewarmed LB ampicillin (100 µg/ml) plate and incubated overnight at 37° C.

Analysis of Positive Clones:

Positive clones were analysed by PCR. Amplification was performed in a GeneAmp 9600 Thermal Cycler (Roche Diagnostic Systems) with PCR mixtures containing 1 µl of purified plasmid DNA extracted from positive clones using the Qiagen Mini Prep Protocol (Qiagen) in a final reaction volume of 25 µl in 10 mM Tris-HCl (pH 8.8), 50 mM KCl, 1.5 mM MgCl2 containing 200 µM of each deoxynucleoside triphosphate, 25 pmol/µl of internal forward and vector reverse primer and 5 U of Taq DNA polymerase (Boehringer Mannheim). Thermal cycling conditions were an initial denaturation of 5 min at 94° C. followed by 30 cycles of 1 min at 94° C., 1 min at 50° C., and 1 min at 72° C. Following amplification the samples were incubated at 72° C. and then held at 4° C. Amplified products were resolved by gel electrophoresis in 1% agarose in Tris acetate buffer, containing 0.5 µg/ml ethidium bromide. Glycerol stocks were made of the positive clones.

Expression of the PCR Product:

For each transformant, 2 ml LB containing 100 µg/ml ampicillin was inoculated with a single E. coli colony and incubated overnight at 37° C. with shaking. 0.1 ml of this overnight culture was added to 10 ml LB containing 100 µg/ml ampicillin. Protein expression was induced by addition of 20, 2, 0.2. and 0.002% L-arabinose and incubated at 37° C. with shaking for 4 h. The culture was pelleted by centrifugation at 5000×G for 10 min and resuspended in 450 µl 10% SDS and 50 µl 10 mM DTT (oxidised). The resuspended pellet was stored at −20° C. until required for processing.

SDS-PA GE Analysis:

Bacterial samples were boiled at 100° C. for 15 min. 12 µl boiled sample was added to 3 µl SDS-PAGE (SDS-polyacrylamide gel electrophoresis) sample buffer and boiled at 100° C. for 5 min. 10 µl was run on a NOVEX gel and run for 35 min at 200 V and then blotted onto PVDF at 25 V for 1 h.

Western Blotting:

The blot was initially blocked in 2% milk powder in PBS containing Tween-20 (MPBST) for 1 h at 37° C. The blot was washed 2×10 min in wash buffer (0.9% (w/v) NaCl, 0.01% Tween-20). The blot was incubated in 1:5000 dilution of anti V5 epitope (Invitrogen) in MPBST for 1 h at room temperature and then washed 3×10 min in wash buffer. The blot was incubated with 1:5000 dilution anti-mouse alkaline phosphatase conjugate (Sigma) in MPBST for 1 h at room temperature and washed 3×10 min in wash buffer. The colour reaction was induced by addition of 1 tablet BCIP/NBT (Sigma) to 10 ml water for <10 min.

MIC Determination by Microtitre Broth Dilution Method

TOP10 E. coli with or without (O) bcrA were grown to a concentration of $2\times10^4$ cfu/ml (bcrA+was grown in the presence of 100 μg/ml ampicillin to select for the pBAD-TOPO vector) in RPMI medium (Sigma) in the presence of 0.002% L-arabinose, as the inducer of the bcrA gene. 100 μl TOP10 E. coli±bcrA was dispensed into 96 well microtitre plate (Sigma) to give a final concentration of 1×104 cfu/ml. Serial doubling dilutions of antibiotic was added to each well, with the concentration ranging from 500 to 0.24 μg/ml. The plates were incubated for 24 h at 37° C. and scored by growth or no growth.

Demonstration of Phage Activity Against Nalidixic Acid

TOP10 E. coli+bcrA were grown to a concentration of $2\times10^4$ cfu/ml in RPMI medium (Sigma) containing 100 μg/ml ampicillin (to select for the pBAD-TOPO vector) in the presence of 0.002% L-arabinose, as the inducer of the bcrA gene. 100 μl TOP10 E. coli+bcrA, at a final concentration of $1\times10^4$ cfu/ml, were dispensed into 96 well microtitre plate (Sigma) in the presence of neat phage and phage diluted 1:10 (see table below). Serial doubling dilutions nalidixic acid was added to each well, with the concentration ranging from 128 to 0.25 μg/ml. A control with just the media was set up. The plates were incubated for 24 h at 37° C. Six phage clones were tested.

Results

Sequencing the bcrA Gene

A 3500 bp sequence of DNA has been identified and sequenced. Within the cloned sequence there was a single open reading frame, which contained the bcrA coding sequence (SEQ ID NO: 1).

Structure and Location of the BcrA Protein

The bcrA sequence contained a single open reading frame which encodes a protein, termed BcrA (SEQ ID NO: 2), of 518 amino acid residues with a predicted molecular weight of 49 kD.

Comparison of the BcrA Protein with the Sequence of Related Efflux Pumps

The BrcA amino acid sequence was aligned with the encoded products of the emrB gene of E. coli and the qacA gene of S. aureus. The results of an identity match using 'align' search (http://www.hgsc.bcm.tmc.edu/searchlauncher) showed that BcrA had homology of 48.8% with the EmrB protein and 20.1% with the QacA protein. It was also found that BrcA has 84.8% homology with the AF 110185 protein of Burkholderia pseudomallei. Laboratory data shows that BrcA is an antibiotic pump. No known ATP binding sites were found in the BcrA amino acid sequence, thus confirming that bcrA gene does not belong to the ATP binding cassette (ABC) transporter family but instead to the MFS family of efflux pumps.

Epitope Mapping of the BcrA Protein

Nonamer peptides showing marked reactivity with sera from Group 4A patients (CF patients infected with Burkholderia cepacia but well) compared with sera from Group 3 patents (CF patients without indications of infection by either B. cepacia or Pseudomonas aeuroginosa) are shown in Table 3. Seven epitopes were indentified from the eptiope mapping experiment, viz. Epitope 1: VISSYS (SEQ ID NO: 11), Epitope 2: ISFGFMA (SEQ ID NO: 12), Epitope 3: MAFFGS (SEQ ID NO: 13), Epitope 4: QTVMGYT (SEQ ID NO: 14), Epitope 5: LRMVASF (SEQ ID NO: 15), Epitope 6: FFVPMTT (SEQ ID NO: 16) and Epitope 7: LLHLSAI (SEQ ID NO: 17).

Phage Antibody Display Library and scFv

Each of the Peptides 1–3 (SEQ ID NOs 18–20) produced two phages with different dominant fingerprints. These were labelled phage 1–6 (with phages 1 and 2 reactive against Peptide 1, phages 3 and 4 reactive against Peptide 2 and phages 5 and 6 reactive against Peptide 3). The phage varied in number in the final panning from 2–4 copies. Phage activity was assessed against the bcrA gene by cloning it into TOP10 E. coli.

Expression of the bcrA Gene in TOP10 E. coli

Western analysis confirmed that the bcrA gene had been cloned into TOP10 E. coli and was being expressed with an apparent weight of about 46 KDa (results not shown).

Antibiotic Resistance Conferred by bcrA in TOP10 E. coli

The minimum inhibitory concentration (MIC) values of the antibiotics tetracycline, chlorohexadine, nalidixic acid and ciprofloxacin against TOP10 E. coli±bcrA are shown in Table 4. No resistance against chlorohexadine and ciprofloxacin was conferred by the bcrA gene in TOP10 E. coli. In contrast, a two well difference in MIC was observed for tetracycline and a three well difference in MIC was observed for nalidixic acid in TOP10 E. coli±bcrA (Table 4).

Phage Activity Against Nalidixic Acid Resistance

Six TOP10 E. coli+bcrA phage clones (phage 1 and 2 reactive against Peptide 1 [SEQ ID NO: 18]; phage 3 and 4 reactive against Peptide 2 [SEQ ID NO: 19]; and phage 5 and 6 reactive against Peptide 3 [SEQ ID NO: 20]) obtained from the panning experiment (supra) were tested for activity against nalidixic acid (Table 5). Compared with the MIC of the control phages (16 μg/ml), four or the six phages showed activity. Activity was most pronounced with Phage 1 (which showed reactivity against Peptide 1 (SEQ ID NO: 18).

Discussion

In bacteria, multi-drug resistance (mdr) pumps were first reported in Staphylococcus aureus (Lomovskaya, O. and Lewis. K., 1992, supra). Simple mdr pumps are also reported in Escherichia coli (emrB) and in Bacillus subtilis (bmr) (Neyfakh, A. A, 1992, Antimicrobial Agents. Chemother., 36: 484–485). The bcrA gene of Burkholderia cepacia belongs to this family of membrane translocases and may protect the cell from antibiotics and other small molecules.

The translated amino acid sequence of the bcrA gene shows high homology with the EmrB protein of E. coli and the QacA protein of S. aureus. Laboratory data shows that the bcrA gene encodes a membrane translocase and belongs to the MFS family of multi-efflux pumps.

The BcrA protein has a typical structure of an integral membrane translocase, with 10 α-helices spanning the membrane. The BcrA protein shows homology with other members of the same family. The protein is a therapeutically and diagnostically useful target, and can be used in active immunisation as a vaccine, as a source of passive immunisation medicaments comprising antibodies specific against it, and in the isolation of therapeutically and diagnostically useful compounds which act against it.

TABLE 1

Description of selected PCR primers

| Oligonucleotide name | Sequence | Description |
|---|---|---|
| EMRN | SEQ ID NO: 3 | Located at the 5' end of the bcrA gene |
| EMRC | SEQ ID NO: 4 | Located at the 3' end of the bcrA gene |
| M13 Forward (−20) | SEQ ID NO: 5 | Vector primer |
| M13 Reverse | SEQ ID NO: 6 | Vector primer |
| BcrA forward | SEQ ID NO: 21 | Located at the 5' end of the bcrA gene |
| BcrA reverse | SEQ ID NO: 22 | Located at the 3' end of the bcrA gene |

All oligonucleotide primers were synthesised by reverse phase HPLC (Genosys Biotechnologies Ltd) using standard phosphoramidite chemistry.

TABLE 2

Transmembrane Domains of the BcrA protein

| Helix | Begin | End | Score | Certainty |
|---|---|---|---|---|
| 1 | 16 | 36 | 1.877 | Certain |
| 2 | 41 | 61 | 1.089 | Certain |
| 3 | 64 | 84 | 1.478 | Certain |
| 4 | 92 | 112 | 1.918 | Certain |
| 5 | 120 | 140 | 0.925 | Putative |
| 6 | 144 | 164 | 2.109 | Certain |
| 7 | 175 | 195 | 1.236 | Certain |
| 8 | 213 | 233 | 1.581 | Certain |
| 9 | 245 | 265 | 0.914 | Putative |
| 10 | 284 | 304 | 2.352 | Certain |
| 11 | 313 | 333 | 1.640 | Certain |
| 12 | 379 | 399 | 1.973 | Certain |
| 13 | 411 | 431 | 0.764 | Putative |
| 14 | 488 | 508 | 1.884 | Certain |

Candidate membrane-spanning segments of the BcrA protein using TopPred 2 (von Heijne, G., 1992, J. Mol. Biol., 2: 287–494). Each of the 10 α-helices is listed, each one being 20 amino acids in length. A score is assigned to each α-helix based on its hydrophobicity and probability of residing within the membrane. From the score, the probability of the sequence being a membrane spanning α-helix is given.

TABLE 3

ELISA results from peptide mapping of BcrA protein

| Peptide | Epitope | Group 1 | Group 2 | Group 3 | Group 4A | Group 4B |
|---|---|---|---|---|---|---|
| 62 | 1 (SEQ ID NO: 11) | 0.950 ± 0.36 | 0.965 ± 0.36 | 0.393 ± 0.08 | 1.284 ± 0.261 | 0.624 ± 0.375 |
| 63 | 1 (SEQ ID NO: 11) | 0.906 ± 0.38 | 1.074 ± 0.56 | 0.377 ± 0.04 | 1.297 ± 0.337 | 0.672 ± 0.412 |
| 64 | 1 (SEQ ID NO: 11) | 0.838 ± 0.36 | 1.071 ± 0.43 | 0.356 ± 0.04 | 1.232 ± 0.251 | 0.704 ± 0.405 |
| 284 | 2 (SEQ ID NO: 12) | 0.981 ± 0.39 | 1.075 ± 0.36 | 0.423 ± 0.05 | 1.220 ± 0.304 | 0.675 ± 0.419 |
| 285 | 2 (SEQ ID NO: 12) | 0.825 ± 0.38 | 1.017 ± 0.35 | 0.375 ± 0.02 | 1.141 ± 0.358 | 0.667 ± 0.338 |
| 286 | 2 (SEQ ID NO: 12) | 0.786 ± 0.37 | 0.915 ± 0.32 | 0.341 ± 0.02 | 1.149 ± 0.404 | 0.718 ± 0.460 |
| 288 | 3 (SEQ ID NO: 13) | 0.931 ± 0.28 | 1.199 ± 0.43 | 0.467 ± 0.02 | 1.595 ± 0.697 | 0.714 ± 0.451 |
| 289 | 3 (SEQ ID NO: 13) | 0.915 ± 0.32 | 1.022 ± 0.32 | 0.432 ± 0.02 | 1.313 ± 0.408 | 0.669 ± 0.434 |
| 290 | 3 (SEQ ID NO: 13) | 0.859 ± 0.39 | 1.103 ± 0.45 | 0.373 ± 0.04 | 1.034 ± 0.274 | 0.679 ± 0.421 |
| 291 | 3 (SEQ ID NO: 13) | 0.898 ± 0.36 | 1.178 ± 0.39 | 0.373 ± 0.03 | 1.108 ± 0.302 | 0.636 ± 0.285 |
| 302 | 4 (SEQ ID NO: 14) | 0.899 ± 0.28 | 1.151 ± 0.37 | 0.452 ± 0.04 | 1.250 ± 0.143 | 0.570 ± 0.342 |
| 303 | 4 (SEQ ID NO: 14) | 0.956 ± 0.32 | 1.135 ± 0.38 | 0.451 ± 0.01 | 1.247 ± 0.141 | 0.654 ± 0.381 |
| 304 | 4 (SEQ ID NO: 14) | 0.971 ± 0.31 | 1.113 ± 0.31 | 0.492 ± 0.03 | 1.399 ± 0.415 | 0.579 ± 0.347 |
| 339 | 5 (SEQ ID NO: 15) | 1.002 ± 0.35 | 1.168 ± 0.37 | 0.430 ± 0.06 | 1.222 ± 0.203 | 0.644 ± 0.337 |
| 340 | 5 (SEQ ID NO: 15) | 1.111 ± 0.43 | 1.256 ± 0.44 | 0.545 ± 0.04 | 1.382 ± 0.210 | 0.727 ± 0.451 |
| 341 | 5 (SEQ ID NO: 15) | 0.946 ± 0.32 | 1.112 ± 0.35 | 0.481 ± 0.01 | 1.352 ± 0.328 | 0.651 ± 0.330 |
| 384 | 6 (SEQ ID NO: 16) | 0.961 ± 0.28 | 1.066 ± 0.31 | 0.475 ± 0.05 | 1.189 ± 0.276 | 0.644 ± 0.278 |
| 385 | 6 (SEQ ID NO: 16) | 0.997 ± 0.26 | 1.202 ± 0.36 | 0.498 ± 0.08 | 1.545 ± 0.390 | 0.713 ± 0.437 |
| 386 | 6 (SEQ ID NO: 16) | 0.807 ± 0.30 | 1.004 ± 0.20 | 0.415 ± 0.03 | 1.152 ± 0.684 | 0.627 ± 0.350 |
| 486 | 7 (SEQ ID NO: 17) | 1.035 ± 0.25 | 1.144 ± 0.25 | 0.520 ± 0.04 | 1.243 ± 0.369 | 0.690 ± 0.379 |
| 487 | 7 (SEQ ID NO: 17) | 0.958 ± 0.38 | 1.059 ± 0.33 | 0.447 ± 0.05 | 1.223 ± 0.250 | 0.666 ± 0.389 |
| 488 | 7 (SEQ ID NO: 17) | 0.897 ± 0.40 | 0.924 ± 0.31 | 0.338 ± 0.03 | 1.296 ± 0.542 | 0.648 ± 0.362 |

GROUP 1: CF patients with Pseudomonas aeuroginosa and Burkholderia cepacia (n = 5)
GROUP 2: CF patients with Pseudomonas aeuroginosa (n = 4)
GROUP 3: CF patients with no Pseudomonas aeuroginosa and Burkholderia cepacia (n = 2)
GROUP 4A: CF patients with Burkholderia cepacia (well) (n = 4)
GROUP 4B: CF patients with Burkholderia cepacia, previously unwell now in hospital (n = 2)

TABLE 4

Growth of TOP10 E. coli bcrA exposed to various antibiotics (μg/ml)

| Antibiotic (μg/ml) | 128 | 64 | 32 | 16 | 8 | 4 | 2 | 1 | 0.5 | 0.25 | 0.125 |
|---|---|---|---|---|---|---|---|---|---|---|---|
| TOP10 E. coli + bcrA | | | | | | | | | | | |
| Tetracycline | − | − | − | − | − | − | + | + | + | + | + |
| Chlorohexadine | − | − | − | − | + | + | + | + | + | + | + |
| Nalidixic Acid | − | − | − | − | + | + | + | + | + | + | + |
| Ciprofloxacin | − | − | − | − | − | − | − | − | − | − | + |
| TOP10 E. coli − bcrA | | | | | | | | | | | |
| Tetracycline | − | − | − | − | − | − | + | + | + | + | + |
| Chlorohexadine | − | − | − | − | + | + | + | + | + | + | + |

TABLE 4-continued

Growth of TOP10 *E. coli* bcrA exposed to various antibiotics (μg/ml)

| Antibiotic (μg/ml) | 128 | 64 | 32 | 16 | 8 | 4 | 2 | 1 | 0.5 | 0.25 | 0.125 |
|---|---|---|---|---|---|---|---|---|---|---|---|
| Nalidixic Acid | – | – | – | – | – | – | + | + | + | + | + |
| Ciprofloxacin | – | – | – | – | – | – | – | – | – | – | + |

TABLE 5

Phage clone activity against resistance of TOP10 *E. coli* + bcrA to nalidixic acid

| Phage | Nalidixic acid MIC (μg/ml) |
|---|---|
| No phage (brcA+) | 16 |
| Phage control | 16 |
| 1 | 2 |
| 2 | 16 |
| 3 | 8 |
| 4 | 16 |
| 5 | 8 |
| 6 | 4 |

---

The invention claimed is:

1. A combined preparation of an inhibitor of a multidrug efflux pump having the sequence of SEQ ID NO: 2 or a multidrug efflux pump having at least 85% homology therewith and at least one antibiotic for simultaneous, separate or sequential use in the treatment of infection by an organism expressing said multidrug efflux pump, wherein said inhibitor comprises an antibody or antigen binding fragment thereof specific against an epitope of said multidrug efflux pump.

2. A combined preparation according to claim 1, the antibiotic or antibiotics being selected from either one of the group consisting a tetracycline and a quinolone.

3. A combined preparation according to claim 2, the quinolone being nalidixic acid.

4. An antimicrobial composition comprising an inhibitor of a multidrug efflux pump having the sequence of SEQ ID NO: 2 or a multidrug efflux pump having at least 85% homology therewith and at least one disinfectant, wherein said inhibitor comprises an antibody or antigen binding fragment thereof specific against an epitope of said multidrug efflux pump.

5. An antimicrobial composition according to claim 4, the disinfectant or disinfectants comprising a quarternary ammonium disinfectant.

6. A method of disinfection comprising applying to a surface to be disinfected an antimicrobial composition according to any one of claims 4–5.

7. A method of forming the antimicrobial composition of claim 4 comprising mixing the inhibitor of the multidrug efflux pump with the disinfectant.

8. The method according to claim 7 wherein said disinfectant comprises a quarternary ammonium disinfectant.

9. A method of treating an individual with an infection with an organism expressing a multidrug efflux pump having the sequence of SEQ ID NO:2 or a multidrug efflux pump having at least 85% homology therewith comprising the step of administering an inhibitor of said multidrug efflux pump wherein said inhibitor comprises an antibody against said multidrug efflux pump or an antigen binding fragment thereof.

10. The method of claim 9, further comprising the step of administering an antibiotic selected from the group consisting of tetracylines and quinolones to the individual.

11. The method according to claim 10, wherein the quinolones comprise nalidixic acid.

12. A method of disinfection comprising applying to a surface to be disinfected an antimicrobial composition comprising an inhibitor of a multidrug efflux pump having the sequence of SEQ ID NO:2 or a multidrug efflux pump having at least 85% homology therewith, wherein said inhibitor comprises an antibody or antigen binding fragment thereof specific against an epitope of said multidrug efflux pump.

13. A method of disinfection comprising applying to a surface to be disinfected an antimicrobial composition comprising an inhibitor of a multidrug efflux pump having the sequence of SEQ ID NO:2 or a multidrug efflux pump having at least 85% homology therewith, wherein said inhibitor comprises an antibody or antigen binding fragment thereof specific against an epitope of said multidrug efflux pump, the antibody or antigen binding fragment thereof being specific against a polypeptide having the sequence of any one of SEQ ID NOS:11–20.

* * * * *